(12) United States Patent
Chan

(10) Patent No.: US 8,657,767 B2
(45) Date of Patent: Feb. 25, 2014

(54) ADJUSTABLE ORTHOPEDIC BOOT

(76) Inventor: Shu-Chen Chan, Fengyuan (TW)

(*) Notice: Subject to any disclaimer, the term of this patent is extended or adjusted under 35 U.S.C. 154(b) by 740 days.

(21) Appl. No.: 12/820,202

(22) Filed: Jun. 22, 2010

(65) Prior Publication Data

US 2011/0313336 A1 Dec. 22, 2011

(51) Int. Cl.
| | |
|---|---|
| *A61F 5/37* | (2006.01) |
| *A61F 13/00* | (2006.01) |
| *A61F 5/00* | (2006.01) |
| *A43B 5/00* | (2006.01) |
| *A43B 1/08* | (2006.01) |
| *A43B 1/06* | (2006.01) |
| *A61F 5/14* | (2006.01) |

(52) U.S. Cl.
USPC ............. 602/16; 128/846; 128/869; 128/882; 602/5; 602/23; 602/27; 602/28; 602/29; 36/84; 36/85; 36/88; 36/86; 36/140

(58) Field of Classification Search
USPC .................. 128/846, 869, 882; 602/5, 16, 23, 602/27–29; 36/84–85, 88–89, 140
See application file for complete search history.

(56) References Cited

U.S. PATENT DOCUMENTS

| | | | | | |
|---|---|---|---|---|---|
| 4,771,768 | A | * | 9/1988 | Crispin | ........................... 602/16 |
| 4,962,760 | A | * | 10/1990 | Jones | .............................. 602/27 |
| 5,092,321 | A | * | 3/1992 | Spademan | ...................... 602/27 |
| 5,676,642 | A | * | 10/1997 | Peters | ............................. 602/27 |
| 5,814,000 | A | * | 9/1998 | Kilbey | ............................ 602/16 |
| 6,155,998 | A | * | 12/2000 | Gilmour | ......................... 602/27 |
| 6,648,843 | B1 | * | 11/2003 | Marciano et al. | ............... 602/27 |
| 7,235,059 | B2 | * | 6/2007 | Mason et al. | ................... 602/26 |
| 7,563,238 | B1 | * | 7/2009 | Breashears | ..................... 602/27 |
| 7,666,157 | B2 | * | 2/2010 | Win | ................................. 602/23 |
| 8,142,381 | B1 | * | 3/2012 | Birnbaum | ....................... 602/23 |
| 2002/0029009 | A1 | * | 3/2002 | Bowman | ......................... 602/27 |
| 2006/0247565 | A1 | * | 11/2006 | Cormier et al. | ................. 602/16 |
| 2009/0099495 | A1 | * | 4/2009 | Campos et al. | ................. 602/27 |

\* cited by examiner

*Primary Examiner* — Patricia Bianco
*Assistant Examiner* — Brandon L Jackson
(74) *Attorney, Agent, or Firm* — Birch, Stewart, Kolasch & Birch, LLP

(57) ABSTRACT

An orthopedic boot has two leg supports connected adjustably to a foot support via two joint assemblies. Each joint assembly has a securing panel, a connecting panel, a guide panel, two limiting members and two holding members. The securing panel is mounted securely on the foot support and has two engaging grooves each having engaging cavities. The connecting panel is mounted securely to one leg support and is pivotally connected to the securing panel. The limiting members has a resilient segment, an engaging pin and a locking tab. The engaging pin is mounted slidably in one of the engaging grooves, engages one of the engaging cavities and selectively abuts the connecting panel. The locking tab is spaced from a periphery of the guide panel to define a locking gap. The holding members are held respectively in the locking gaps and abut respectively against the locking tabs.

16 Claims, 8 Drawing Sheets

ADJUSTABLE ORTHOPEDIC BOOT

BACKGROUND OF THE INVENTION

1. Field of the Invention

The present invention relates to an orthopedic boot, and more particularly to an adjustable orthopedic boot.

2. Description of Related Art

An orthopedic boot is always use to hold a twisted ankle or broken leg at a fixed position during a rehabilitating process. A conventional orthopedic boot substantially comprises a foot support and two leg supports. The leg supports are mounted securely and respectively on two sides of the foot support to hold a leg of a user at a fixed angle relative to his/her foot.

However, the leg supports of the conventional orthopedic boot is unadjustable to the foot support, so the leg of the user can only be held at a fixed angle relative to the foot during the rehabilitation. Therefore, the leg of the user cannot move or rotate relative to the foot during wearing the conventional orthopedic boot on, but this will reduce the rehabilitation effect to the injured ankle or leg. The conventional orthopedic boot is not versatile in use.

To overcome the shortcomings, the present invention tends to provide an orthopedic boot to mitigate or obviate the aforementioned problems.

SUMMARY OF THE INVENTION

The main objective of the invention is to provide an orthopedic boot that has leg supports pivotable relative to a foot support to make the orthopedic boot adjustable and versatile in use.

The orthopedic boot has a foot support, two leg supports and two joint assemblies. The leg supports are respectively connected adjustably to the foot support via the joint assemblies. Each joint assembly is mounted between the foot support and a corresponding one of the leg supports and has a securing panel, a connecting panel, a guide panel, two limiting members and two holding members. The securing panel is mounted securely on the foot support and has two curved engaging grooves. Each engaging groove has multiple engaging cavities formed in and along an inner surface of the engaging groove. The connecting panel is mounted securely to a corresponding leg support and is pivotally connected to the securing panel. The guide panel is mounted securely on the foot support and has a curved guiding groove aligning with the engaging grooves in the securing panel. The limiting members are resilient and are pivotally mounted on the connecting panel. Each limiting member has a pivoting end, a locking end, a resilient segment, an engaging pin and a locking tab. The pivoting end is connected pivotally to the connecting panel. The locking end is opposite to the pivoting end. The resilient segment is formed between the pivoting end and the locking end. The engaging pin is mounted at a position between the resilient segment and the locking end, is mounted slidably in one of the engaging grooves in the securing panel, engages one of the engaging cavities in a corresponding engaging groove and selectively abuts the connecting panel. The locking tab is formed on and protrudes from the locking end of the resilient member and is spaced from a periphery of the guide panel to define a locking gap between the locking tab and the periphery of the guide panel. The holding members are mounted slidably on the guide panel along the guiding groove, are held respectively in the locking gaps between the periphery of the guide panel and the locking tabs and abut respectively against the locking tabs on the limiting members.

Other objects, advantages and novel features of the invention will become more apparent from the following detailed description when taken in conjunction with the accompanying drawings.

DETAILED DESCRIPTION OF PREFERRED EMBODIMENT

Figure 1:
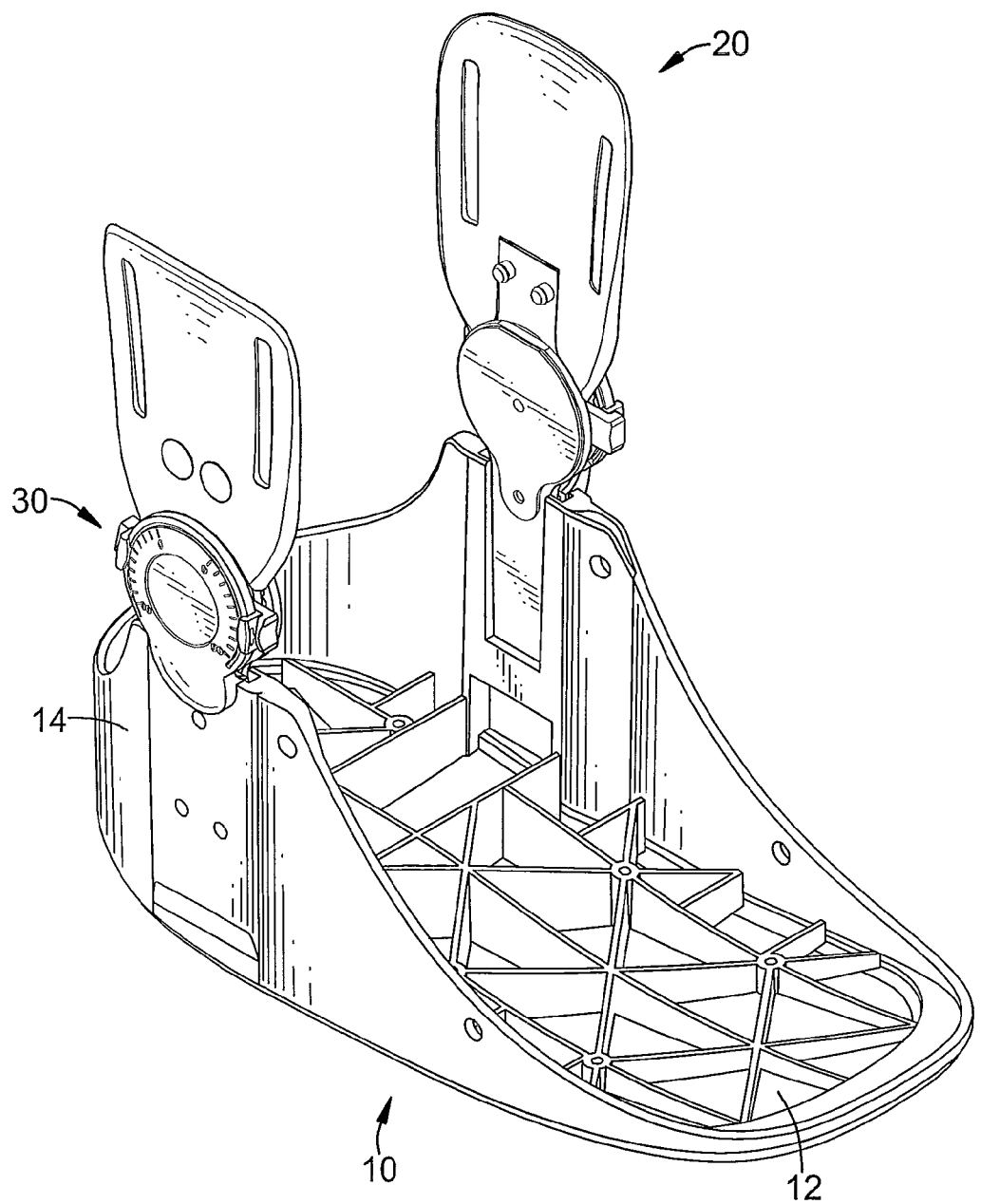
FIG. 1 is a perspective view of an orthopedic boot in accordance with the present invention.
Figure 2:
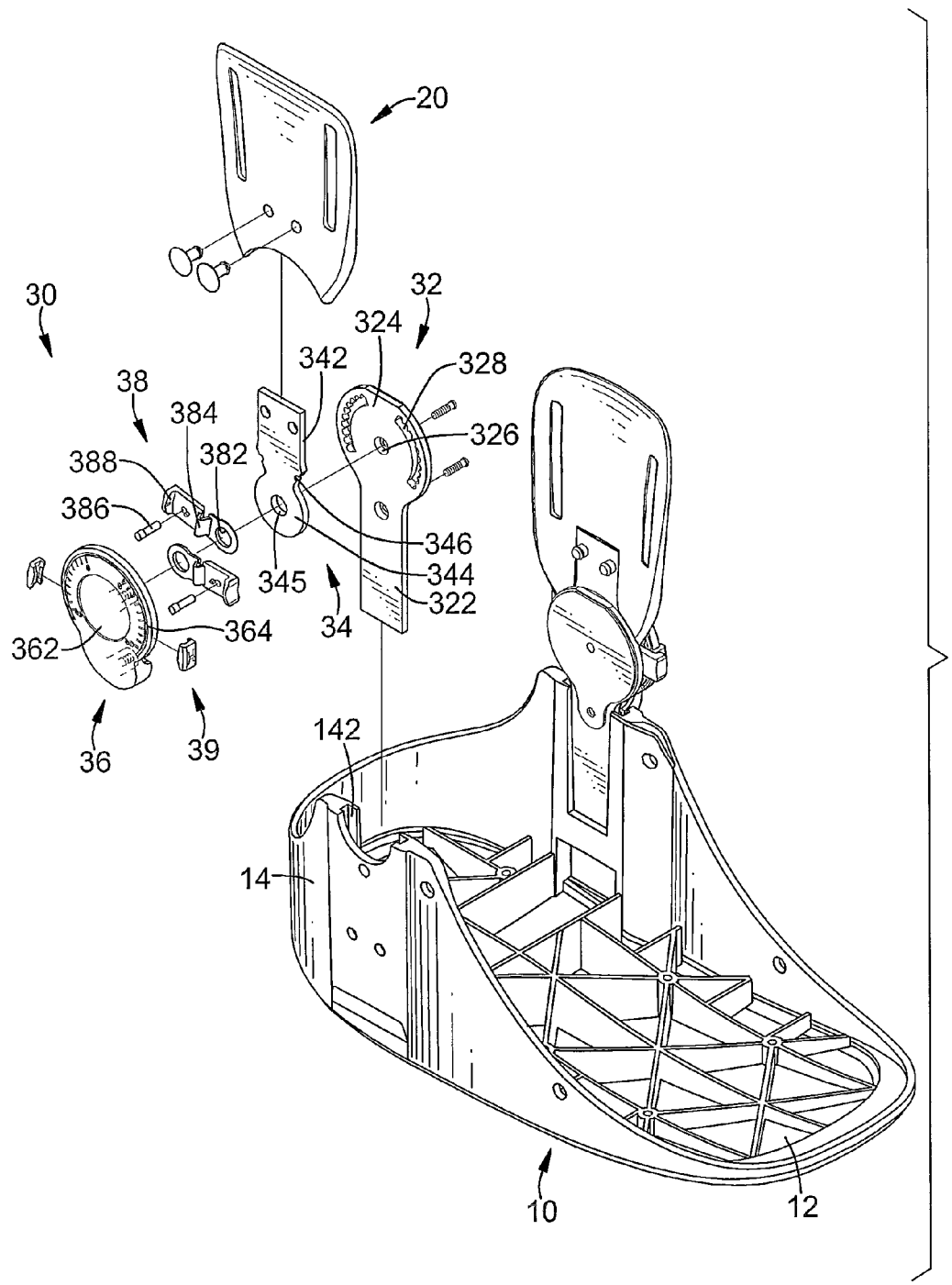
FIG. 2 is a partially exploded perspective view of the orthopedic boot in FIG. 1.
Figure 3:
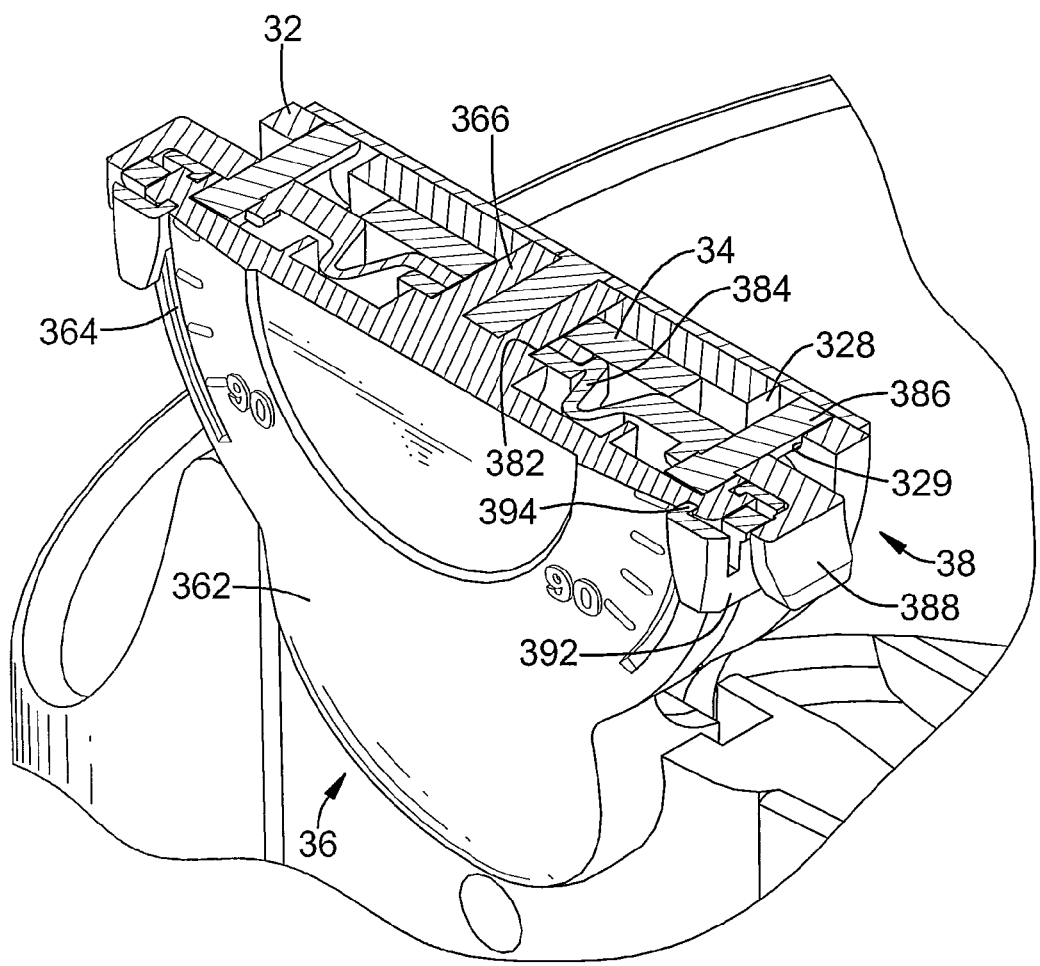
FIG. 3 is an enlarged partial perspective view in partial section of the orthopedic boot in FIG. 1.

With reference to FIGS. 1 to 3, an orthopedic boot in accordance with the present invention comprises a foot support 10, two leg supports 20 and two joint assemblies 30.

The foot support 10 may have a U-shaped cross section and comprises a sole segment 12 and two side walls 14. The side walls 14 are formed on and protrude from the top of the sole segment 12 respectively from two side edges of the sole segment 12. Each side wall 14 has an inner side and a securing channel 142. The inner sides of the side walls 14 face to each other. The securing channel 142 is defined longitudinally in the inner side of the side wall 14.

The leg supports 20 are respectively connected adjustably to the side walls 14 of the foot support 10 via the joint assemblies 30.

Each joint assembly 30 is mounted between one of the side walls 14 of the foot support 10 and a corresponding one of the leg supports 20. Each joint assembly 30 comprises a securing panel 32, a connecting panel 34, a guide panel 36, two resilient limiting members 38 and two holding members 39.

Figure 4:
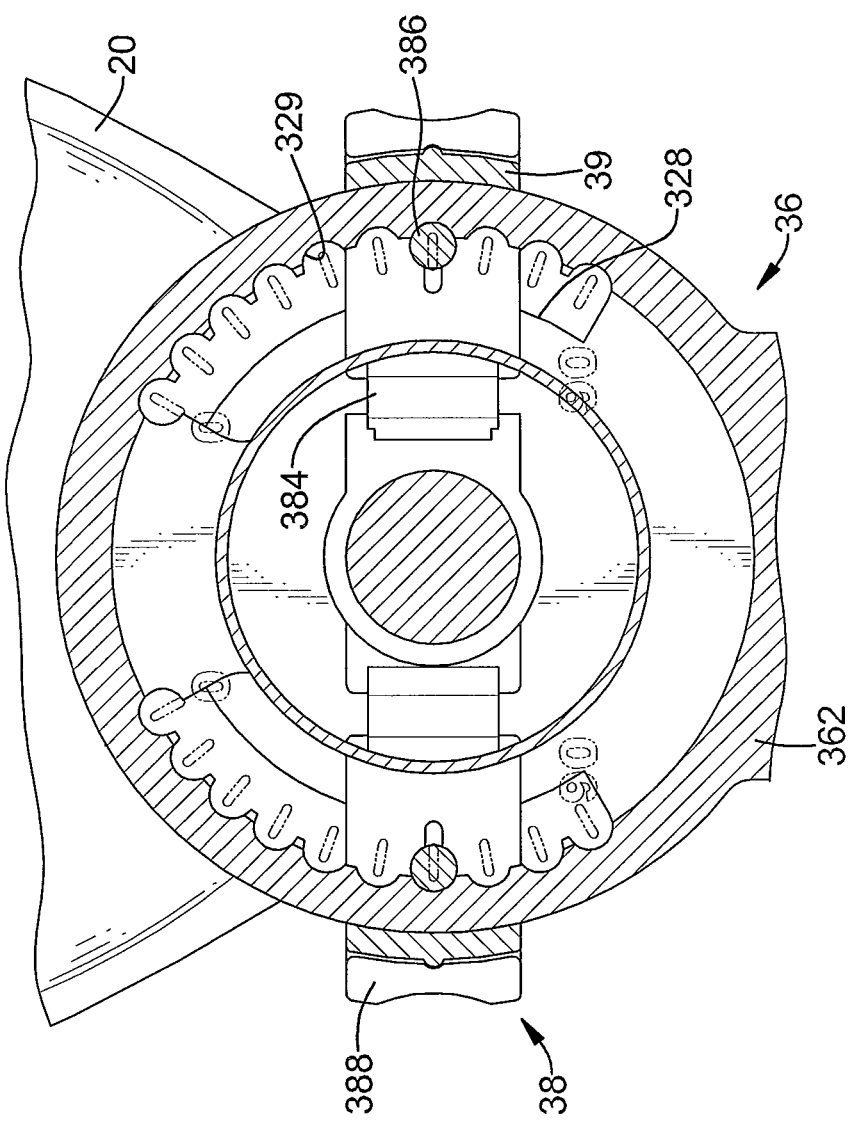
FIG. 4 is an enlarged side view in partial section of the orthopedic boot in FIG. 1.
Figure 5:
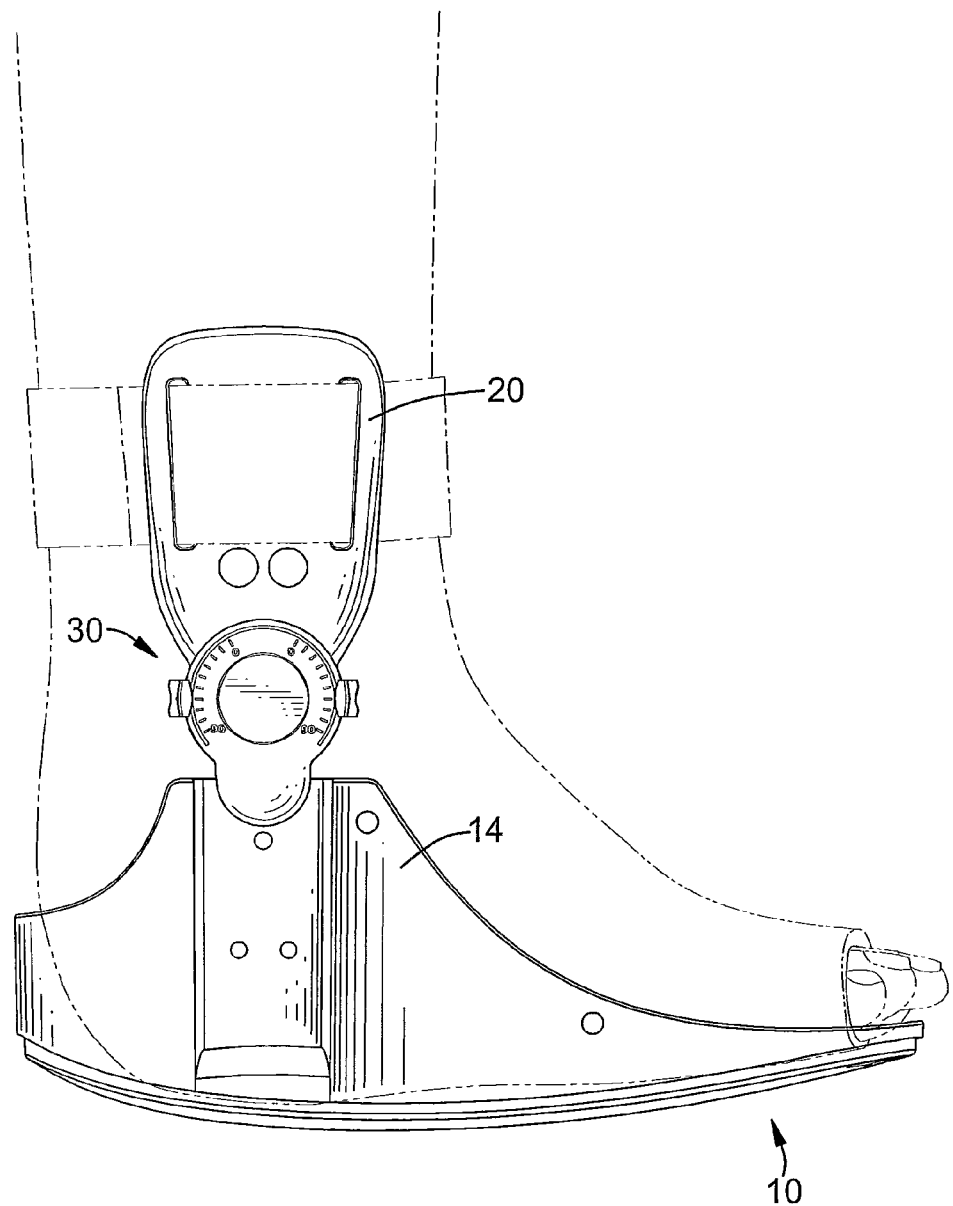
FIG. 5 is an operational side view of the orthopedic boot in FIG. 1 being in use.
Figure 6:
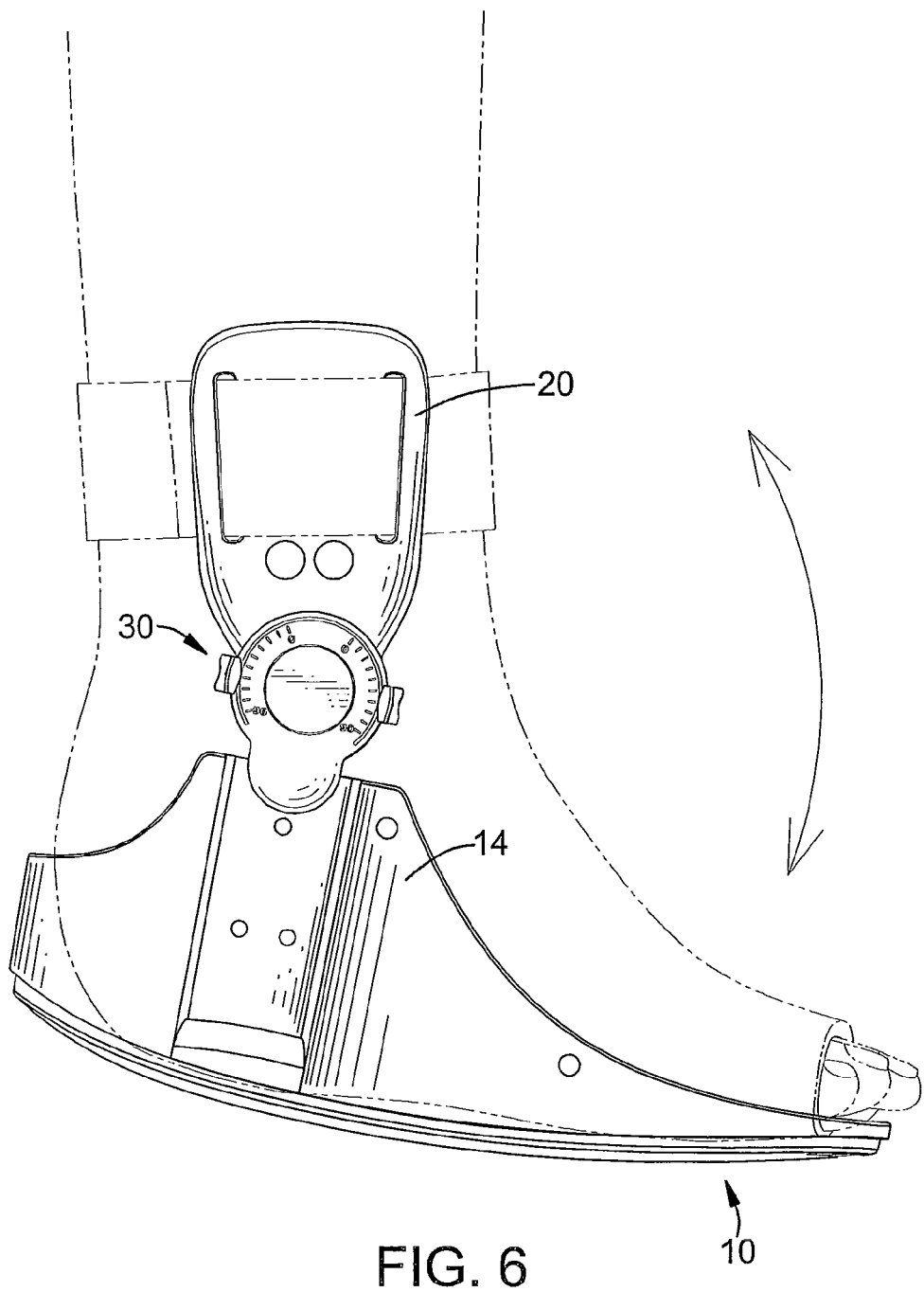
FIG. 6 is an operational side view of the orthopedic boot in FIG. 1 showing an ankle of a user being allowed to move at a desired angle range.

With further reference to FIG. 4, the securing panel 32 is mounted securely on a corresponding side wall 14 of the foot support 10, may be mounted securely in the securing channel 142 in the corresponding side wall 14 and comprises a securing segment 322 and a pivotal segment 324. The securing segment 322 is held securely in the securing channel 142 in the corresponding side wall 14, may be rectangular and has a top. The pivotal segment 324 is formed on and connected to the top of the securing segment 322, may be circular and has a center, a pivotal hole 326 and two engaging grooves 328. The pivotal hole 326 is defined through the center of the pivotal segment 324. The engaging grooves 328 are curved and defined through the pivotal segment 324 around the pivotal hole 326 and have a center at the pivotal hole 326. Each engaging groove 328 has an inner surface and multiple engaging cavities 329 formed in and along the inner surface.

The connecting panel 34 is mounted securely to a corresponding leg support 20, is pivotally connected to the securing panel 32 and has a mounting segment 342, a pivotal segment 344 and two limiting segments 346. The mounting segment 342 is connected securely to the corresponding leg support 20, may be rectangular and has a bottom. The pivotal segment 344 is formed on and connected to the bottom of the mounting segment 342, may be circular and has a center and a pivotal hole 345. The pivotal hole 345 is defined through the center of the pivotal segment 344 and aligns with the pivotal hole 326 in the securing panel 32. The limiting segments 346 are defined between the mounting segment 342 and the pivotal segment 344 respectively at two sides of the connecting panel 34 and may be two recesses.

The guide panel 36 is mounted securely on the corresponding side wall 14 and has a circular guiding segment 362 and a guiding groove 364. The guiding segment 362 is aligned with and corresponds to the pivotal segments 324,344 on the securing and connecting panels 32,34 in shape and position and has a periphery. The guiding groove 364 is curved, is formed in the guiding segment 362 and aligns with the engaging grooves 328 in the securing panel 32. The guide panel 36 may further has marks formed on the guiding segment along the guiding groove 364 to provide an index effect to the user.

The limiting members 38 are resilient and are pivotally connected to the pivotal segment 344 of the connecting panel 34, and the connecting panel 34 are located between and squeezed by the securing panel 32 and the limiting members 38. Each limiting member 38 has a pivoting end, a locking end, a middle, a pivoting hole 382, a resilient segment 384, an engaging pin 386 and a locking tab 388. The pivoting end is connected pivotally to the connecting panel 34, and the locking end is opposite to the pivoting end. The pivoting hole 382 is defined through the pivoting end and is aligned with the pivoting hole 382 in the other limiting member 38 and the pivotal hole 345 in the connecting panel 34. A pivotal pin 366 is mounted through the pivoting holes 382 in the limiting members 38 and the pivotal holes 345,326 in the connecting and securing panels 34,32 to pivotally connect the limiting members 38 and the connecting and securing panels 32,34 together. Additionally, the pivotal pin 366 may be a separate part from the others and may be integrally formed on and protrude from the guide panel 36, such that the limiting members 38 are connected pivotally to the guide panel 36 also.

The middle of the limiting member 38 is formed between the pivoting end and the locking end. The resilient segment 384 is formed on the middle to make the locking end expandable and retractable relative to the pivoting end. The engaging pin 386 is mounted at a position between the resilient segment 384 and the locking end, is mounted slidably in one of the engaging grooves 328 in the securing panel 32, engages one of the engaging cavities 329 in the corresponding engaging groove 328 and selectively abuts one of the limiting segments 346 on the connecting panel 34. The locking tab 388 is formed on and protrudes from the locking end of the resilient member 38 and is spaced from the periphery of the guiding segment 362 of the guide panel 36 to define a locking gap between the locking tab 388 and the periphery of the guiding segment 362.

The holding members 39 are mounted slidably on the guiding segment 362 of the guide panel 36 along the guiding groove 364, are held respectively in the locking gaps between the periphery of the guiding segment 362 and the locking tabs 388 and abut respectively against the locking tabs 388 on the limiting members 38. Each holding member 39 has a U-shaped cross section, an abutting segment 392 and a lip 394. The abutting segment 392 abuts against a corresponding locking tab 388 to hold the limiting members 38 at locked conditions to prevent the limiting members 38 from rotating. The lip 394 is formed on one end of the holding member 39 and is mounted slidably in the guiding groove 364.

In use, with reference to FIGS. 2, 3, 5 and 6, because the connecting panels 34 that are connected securely to the leg supports 20 are pivotally connect to the securing panels 32 that are connected securely to the foot support 10, the leg supports 20 is pivotable relative to the foot support 10. With the abutting segments 392 of the holding members 39 abutting against the locking tabs 388 on the limiting members 38, the limiting members 38 can be kept from rotating and held securely at positions relative to the securing panel 32 and the guide panel 36. At this time, the engaging pins 386 on the limiting members 38 engage the engaging cavities 329 in the engaging grooves 328 of the securing panel 32. Accordingly, the engaging pins 386 can provide a limiting effect to allow the connecting panel 34 pivoting relative to the securing panel 32 until one of the limiting segments 346 abutting with a corresponding one of the engaging pins 386. Therefore, the leg supports 20 is pivotable relative to the foot support 10 at a limited angular range to allow the legs of a user can move or pivot at the limited range, such that the rehabilitation effect provided by the orthopedic boot can be improved.

Figure 7:
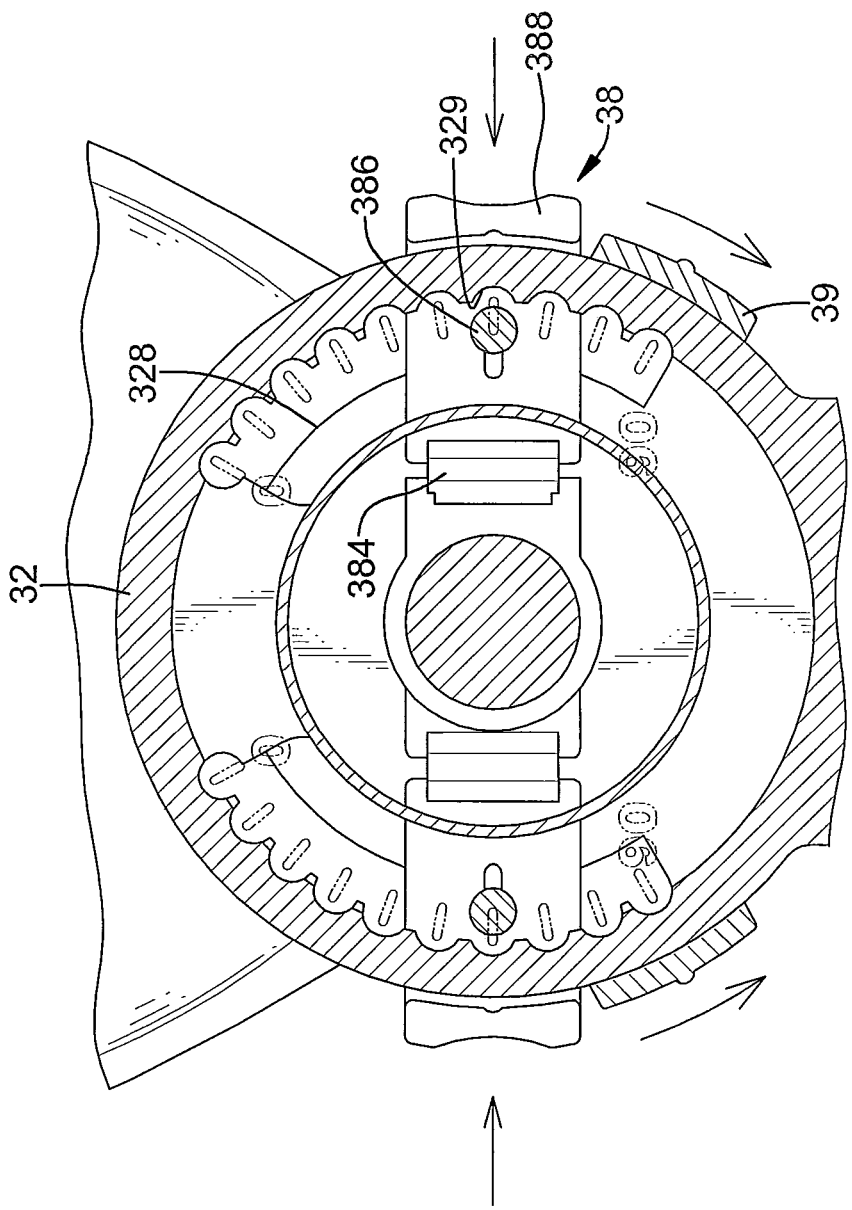
FIG. 7 is an operational side view in partial section of the joint assembly of the orthopedic boot in FIG. 1 to adjust the pivotal angle range between the leg support and the foot support.
Figure 8:
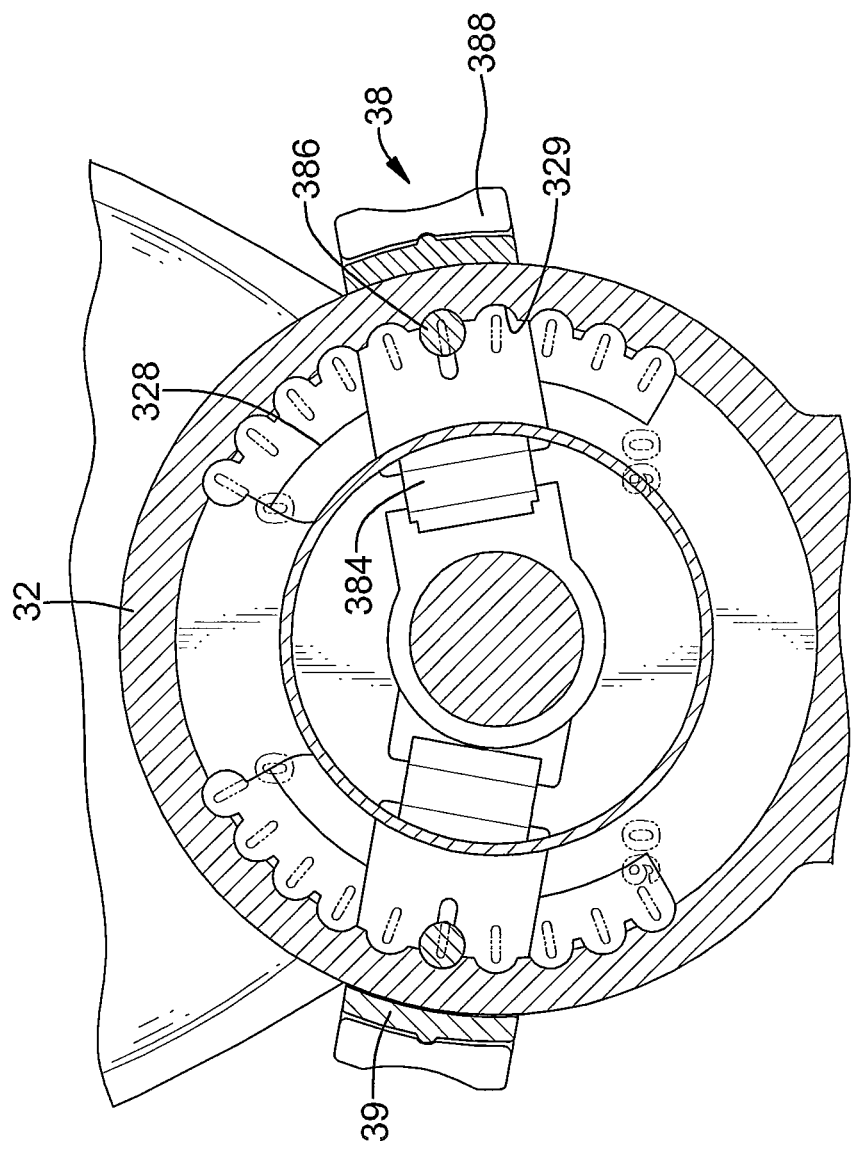
FIG. 8 is an operational side view in partial section of the orthopedic boot in FIG. 1 showing the pivotal angle range between the leg support and the foot support being adjusted.

To adjust the pivotal angle range between the leg supports 20 and the foot support 10, with further reference to FIGS. 7 and 8, the holding members 39 are moved along the guiding channel 364 and are escaped from the limiting gaps between the periphery of the guiding segment 362 of the guide panel 36 and locking tabs 388. Consequently, the limiting members 38 are unlocked and can be pressed at the locking tabs 388 to make the engaging pin 386 disengaging from the corresponding engaging cavities 329. Thus, the limiting members 38 can be pivoted to move along the engaging grooves 328 to make the engaging pins 386 aligning with another engaging cavities 329. The engaging pins 386 can engage automatically the aligning engaging cavities 329 with the resilient force provided by the resilient segments 384 after the locking tabs 388 being released. After the limiting members 38 being moved to desired positions, the holding members 39 are moved into the locking gaps between the periphery of the guiding segment 326 and the locking tabs 388 to hold the limiting members 38 at the new desired positions securely. Accordingly, the pivotal range of the leg supports 20 relative to the foot support 10 can be adjusted and changed to fit with different needs of the user, and the use and operation of the orthopedic boot is versatile.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:
1. An orthopedic boot comprising:
a foot support; and
two leg supports are respectively connected adjustably to the foot support via two joint assemblies, wherein
each joint assembly is mounted between the foot support and a corresponding one of the leg supports and comprising
a securing panel mounted securely on the foot support and having two curved engaging grooves each having multiple engaging cavities formed in and along an inner surface of the engaging groove;

a connecting panel mounted securely to a corresponding leg support and pivotally connected to the securing panel;
a guide panel mounted securely on the foot support and having a curved guiding groove aligning with the engaging grooves in the securing panel;
two limiting members being resilient and pivotally mounted on the connecting panel, and each limiting member having
   a pivoting end connected pivotally to the connecting panel;
   a locking end opposite to the pivoting end;
   a resilient segment formed between the pivoting end and the locking end;
   an engaging pin mounted at a position between the resilient segment and the locking end, mounted slidably in one of the engaging grooves in the securing panel, engaging one of the engaging cavities in a corresponding engaging groove and selectively abutting the connecting panel; and
   a locking tab formed on and protruding from the locking end of the resilient member and being spaced from a periphery of the guide panel to define a locking gap between the locking tab and the periphery of the guide panel; and
two holding members mounted slidably on the guide panel along the guiding groove, held respectively in the locking gaps between the periphery of the guide panel and the locking tabs and abutting respectively against the locking tabs on the limiting members, wherein
each holding member of each joint assembly has
   a U-shaped cross section;
   an abutting segment abutting against the locking tab on a corresponding limiting member of the joint assembly to hold the corresponding limiting member at a locked condition; and
   a lip formed on one end of the holding member and is mounted slidably in the guiding groove in the guide panel of the joint assembly.

2. The orthopedic boot as claimed in claim 1, wherein
the foot support may have a U-shaped cross section and comprises a sole segment and two side walls formed on and protruding from a top of the sole segment respectively from two side edges of the sole segment;
the leg supports are pivotally connected respectively to the side walls of the foot support via the joint assemblies; and
the securing panel and the guide panel of each joint assembly are mounted securely on a corresponding one of the side walls of the foot support.

3. The orthopedic boot as claimed in claim 2, wherein
each side wall of the foot support has a securing channel defined longitudinally in the side wall at an inner side facing to the other side wall; and
the securing panel of each joint assembly is mounted securely in the securing channel in the corresponding side wall.

4. The orthopedic boot as claimed in claim 3, wherein the securing panel of each joint assembly comprises
a securing segment held securely in the securing channel in the corresponding side wall and having a top; and
a pivotal segment formed on and connected to the top of the securing segment and having a center and a pivotal hole defined through the center of the pivotal segment, wherein the engaging grooves are defined through the pivotal segment around the pivotal hole and have a center at the pivotal hole.

5. The orthopedic boot as claimed in claim 4, wherein the connecting panel of each joint assembly has
   a mounting segment connected securely to a corresponding one of the leg supports and having a bottom; and
   a pivotal segment formed on and connected to the bottom of the mounting segment and has a center and a pivotal hole defined through the center of the pivotal segment and aligning with the pivotal hole in the securing panel;
   each limiting member of each joint assembly has a pivoting hole defined through the pivoting end of the limiting member and aligned with the pivoting hole in the other limiting member and the pivotal hole in the connecting panel of the joint assembly; and
   each joint assembly further has a pivotal pin mounted through the pivoting holes in the limiting members and the pivotal holes in the connecting and securing panels of the joint assembly to pivotally connect the limiting members and the connecting and securing panels together.

6. The orthopedic boot as claimed in claim 5, wherein the pivotal pin of each joint assembly is integrally formed on and protrudes from the guide panel of the joint assembly.

7. The orthopedic boot as claimed in claim 6, wherein the connecting panel of each joint assembly further has two limiting segments defined between the mounting segment and the pivotal segment respectively at two sides of the connecting panel and selective abutting the engaging pins on the limiting members of the joint assembly.

8. The orthopedic boot as claimed in claim 7, wherein
the guide panel of each joint assembly has a guiding segment aligned with and corresponding to the pivotal segments on the securing and connecting panels in shape and position; and
the guiding groove in the guide panel of each joint assembly and the periphery for defining the locking gap with the locking tab of a corresponding limiting member in the guide panel are formed in the guiding segment of the guide panel.

9. The orthopedic boot as claimed in claim 1, wherein the securing panel of each joint assembly comprises
a securing segment connected securely to the foot support and having a top; and
a pivotal segment formed on and connected to the top of the securing segment and having a center and a pivotal hole defined through the center of the pivotal segment, wherein the engaging grooves are defined through the pivotal segment around the pivotal hole and have a center at the pivotal hole.

10. The orthopedic boot as claimed in claim 9, wherein the connecting panel of each joint assembly has
   a mounting segment connected securely to a corresponding one of the leg supports and having a bottom; and
   a pivotal segment fowled on and connected to the bottom of the mounting segment and has a center and a pivotal hole defined through the center of the pivotal segment and aligning with the pivotal hole in the securing panel;
   each limiting member of each joint assembly has a pivoting hole defined through the pivoting end of the limiting member and aligned with the pivoting hole in the other limiting member and the pivotal hole in the connecting panel of the joint assembly; and
   each joint assembly further has a pivotal pin mounted through the pivoting holes in the limiting members and the pivotal holes in the connecting and securing panels of the joint assembly to pivotally connect the limiting members and the connecting and securing panels together.

11. The orthopedic boot as claimed in claim 10, wherein the pivotal pin of each joint assembly is integrally formed on and protrudes from the guide panel of the joint assembly.

12. The orthopedic boot as claimed in claim 11, wherein the connecting panel of each joint assembly further has two limiting segments defined between the mounting segment and the pivotal segment respectively at two sides of the connecting panel and selective abutting the engaging pins on the limiting members of the joint assembly.

13. The orthopedic boot as claimed in claim 12, wherein
the guide panel of each joint assembly has a guiding segment aligned with and corresponding to the pivotal segments on the securing and connecting panels in shape and position; and
the guiding groove in the guide panel of each joint assembly and the periphery for defining the locking gap with the locking tab of a corresponding limiting member in the guide panel are formed in the guiding segment of the guide panel.

14. The orthopedic boot as claimed in claim 1, wherein
the connecting panel of each joint assembly has
a mounting segment connected securely to a corresponding one of the leg supports and having a bottom; and
a pivotal segment formed on and connected to the bottom of the mounting segment and pivotally connected to the securing panel of the joint assembly.

15. The orthopedic boot as claimed in claim 14, wherein the connecting panel of each joint assembly further has two limiting segments defined between the mounting segment and the pivotal segment respectively at two sides of the connecting panel and selective abutting the engaging pins on the limiting members of the joint assembly.

16. The orthopedic boot as claimed in claim 1, wherein
the guide panel of each joint assembly has a guiding segment pivotally connected to the securing and connecting panel; and
the guiding groove in the guide panel of each joint assembly and the periphery for defining the locking gap with the locking tab of a corresponding limiting member in the guide panel are formed in the guiding segment of the guide panel.

* * * * *